United States Patent
Holmes

(10) Patent No.: US 8,978,468 B2
(45) Date of Patent: Mar. 17, 2015

(54) NONVISUAL INDICATION OF AN UNWANTED CHEMICAL IN AN INGESTIBLE SUBSTANCE

(71) Applicant: Stephen F. Holmes, Portland, OR (US)

(72) Inventor: Stephen F. Holmes, Portland, OR (US)

(*) Notice: Subject to any disclaimer, the term of this patent is extended or adjusted under 35 U.S.C. 154(b) by 0 days.

(21) Appl. No.: 14/517,730

(22) Filed: Oct. 17, 2014

(65) Prior Publication Data

US 2015/0033825 A1 Feb. 5, 2015

Related U.S. Application Data

(63) Continuation-in-part of application No. 12/907,969, filed on Oct. 19, 2010, now abandoned.

(60) Provisional application No. 61/253,048, filed on Oct. 19, 2009.

(51) Int. Cl.
  *G01N 33/02* (2006.01)
  *G01N 33/14* (2006.01)
  *G01N 33/00* (2006.01)
  *G01N 31/22* (2006.01)

(52) U.S. Cl.
  CPC ............. *G01N 33/02* (2013.01); *G01N 33/14* (2013.01); *G01N 33/0001* (2013.01); *G01N 31/22* (2013.01)
  USPC ........................................... 73/432.1

(58) Field of Classification Search
  CPC ...................................... G01N 33/14
  USPC ............................................ 73/61.41
  See application file for complete search history.

(56) References Cited

U.S. PATENT DOCUMENTS

| 2005/0133420 A1* | 6/2005 | Rinker et al. | 210/143 |
| 2009/0197283 A1* | 8/2009 | Gold et al. | 435/7.9 |
| 2011/0053173 A1* | 3/2011 | Hood et al. | 435/7.1 |

* cited by examiner

*Primary Examiner* — Paul West
(74) *Attorney, Agent, or Firm* — Kolisch Hartwell, P.C.

(57) ABSTRACT

Methods and systems for detecting and indicating the presence of undesirable substances in ingestible substance such as food or beverages. More specifically, systems and methods for nonvisually and concealably indicating and detecting the presence of unwanted or undesired drugs in beverages and/or food.

14 Claims, 2 Drawing Sheets

NONVISUAL INDICATION OF AN UNWANTED CHEMICAL IN AN INGESTIBLE SUBSTANCE

CROSS-REFERENCE TO RELATED APPLICATIONS

This application is a continuation-in-part of U.S. patent application Ser. No. 12/907,969, filed Oct. 19, 2010 and entitled "Nonvisual Indication of an Unwanted Chemical in an Ingestible Substance", which in turn claims the benefit under 35 U.S.C. §119(e) of U.S. Provisional Patent Application Ser. No. 61/253,048, filed Oct. 19, 2009 and entitled "Methods and Systems for Performing a Concealed Test to Determine the Presence of an Unwanted Drug in a Beverage", the disclosures of each of which are herein incorporated by reference.

BACKGROUND

The present invention relates to methods and systems for detecting and indicating the presence of undesirable substances in ingestible substance such as food or beverages. More specifically, the invention relates to systems and methods for nonvisually and concealably indicating and detecting the presence of unwanted or undesired drugs in a beverage or food.

Certain drugs, sometimes referred to as "date rape drugs," have been used to facilitate sexual assaults on unsuspecting victims. Typically the drug is surreptitiously placed in the intended victim's beverage or food. This is a relatively easy process because this class of drug typically provides little or no indication of its presence, creating little or no color change, detectable smell, or change in flavor in the drugged substance that could detected by the intended victim. Once consumed, the drugs typically used for this purpose can create weakness, confusion, and/or unconsciousness in the victim, who typically has no memory of what transpired while they were drugged. Some of these drugs, when combined with alcohol consumption, may exhibit an even more pronounced sedating effect.

While the victim is unconscious or disoriented, they may be subjected to sexual assault, theft, or other abuses by the person who drugged them.

Some pharmaceuticals which have been used as date rape drugs include flunitrazepam (trade name ROHYPNOL, and street name "roofie"), gamma-hydroxybutyric acid (or GHB), and ketamine. Similar acting drugs may also be used as date rape drugs, such as clonazepam (trade name KLONOPIN in the U.S. and RIVOTRIL in Mexico), alprazolam (trade name XANAX), and other benzodiazepines including temazepam (trade name RESTORIL) and midazolam.

Currently available tests for the detection of such drugs focus on creating a visible indicator that that the drug is present. Selected testing methods and systems are described in (a) U.S. Pat. Nos. 4,992,296; 5,457,054; 6,153,147; 6,703,216; 6,713,306; and 7,238,533; (b) U.S. patent application Nos. US2001/0046710; US2003/0026731; US2003/0224474; US2004/0146429; US2007/0065338; US2007/0099300; US2008/0006600; US2008/0102482; and US2009/0196675; (c) PCT Patent Application No. WO2005/059541; and (d) U.K. Patent No. 2436362, all of which are incorporated herein by reference.

The above types of tests are typical, in that they involve a tester device that, when exposed to a liquid, exhibits a visual color change when a target drug is present in the liquid. See for example U.S. Pat. No. 7,238,533, which discloses a color change in applied finger nail polish; U.S. Patent Application Publication No. 2004/0146429, which discloses an embedded so-called colorimetric indicator in a porous material used as a cocktail napkin, coaster, placemat, menu, matchbook, drink carrier, flyer, coupon, personal test kit or business card; and U.S. Patent Application Publication No. 2007/0099300, which discloses a color change on a straw. These tests, however, may not be readily concealable, as each test requires a visual analysis in order to determine the results of the test. Opportunities for testing may therefore be limited in a social setting and in the presence of the person who is suspected of placing an unwanted drug in a beverage.

What is needed is a test system that can verify the presence or absence of a target drug in a food or beverage without requiring a visual evaluation, so that the person suspected of tampering with the food or beverage need never know that they are under suspicion.

BRIEF SUMMARY

In one embodiment, the invention includes a non-visual verification method that includes selecting an ingestible substance, using a detector on the selected, ingestible substance, and non-visually indicating whether a target substance is present in the ingestible substance.

In another embodiment, the invention includes a non-visual verification method that includes selecting an ingestible substance; making a detector for non-visual display of whether a target substance is present in the selected, ingestible substance; operating the detector and non-visually indicating whether a target substance is present in the ingestible substance.

In yet another embodiment, the invention is characterized as a non-visual verification system, where the non-visual verification system includes a non-visual, sensing mechanism constructed to verify whether a target drug is present in an ingestible substance by producing a non-visual indicator that can be understood by a user.

In yet another embodiment, the invention is characterized as a non-visual verification device, where the non-visual verification device includes a non-visual, sensing component constructed to verify whether a target drug is present in an ingestible substance by producing a non-visual indicator that can be understood by a user.

DETAILED DESCRIPTION

The present invention includes systems and methods for performing a non-visual test to determine the presence of a target substance in an ingestible substance. In particular, the invention includes systems and methods for performing a non-visual test to determine the presence of a target substance in an ingestible substance, where the target substance may be indicated both non-visually and concealably.

Figure 1:
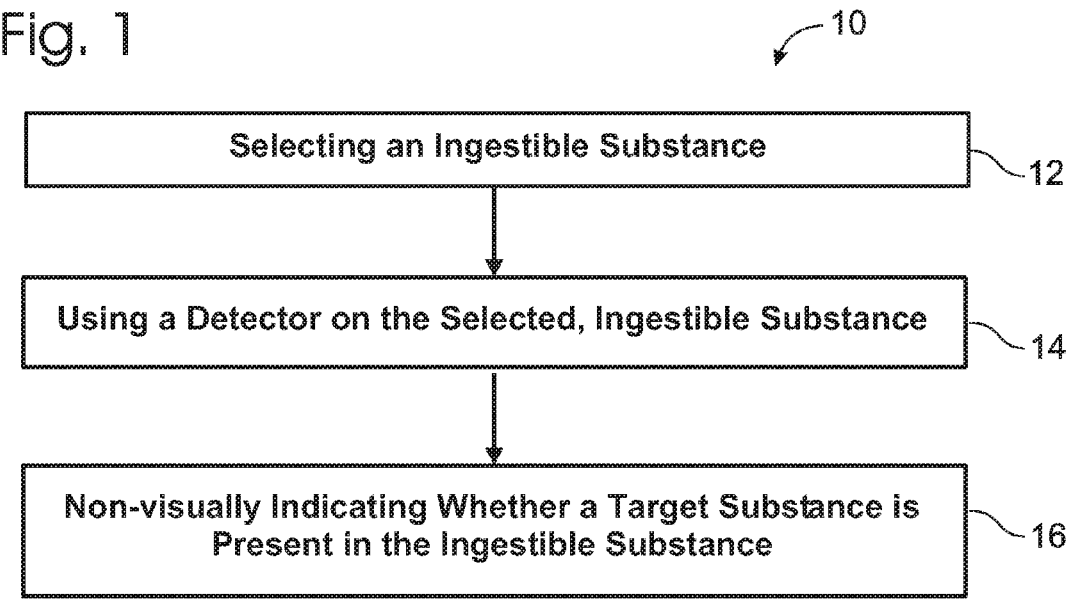
FIG. 1 is a flowchart depicting a non-visual verification method, according to a selected embodiment of the invention.

One embodiment of the present method is depicted as flowchart 10 in FIG. 1. The method includes selecting an ingestible substance, at 12; using a detector on the selected, ingestible substance, at 14; and non-visually indicating whether a target substance is present in the ingestible substance, at 16.

Figure 2:
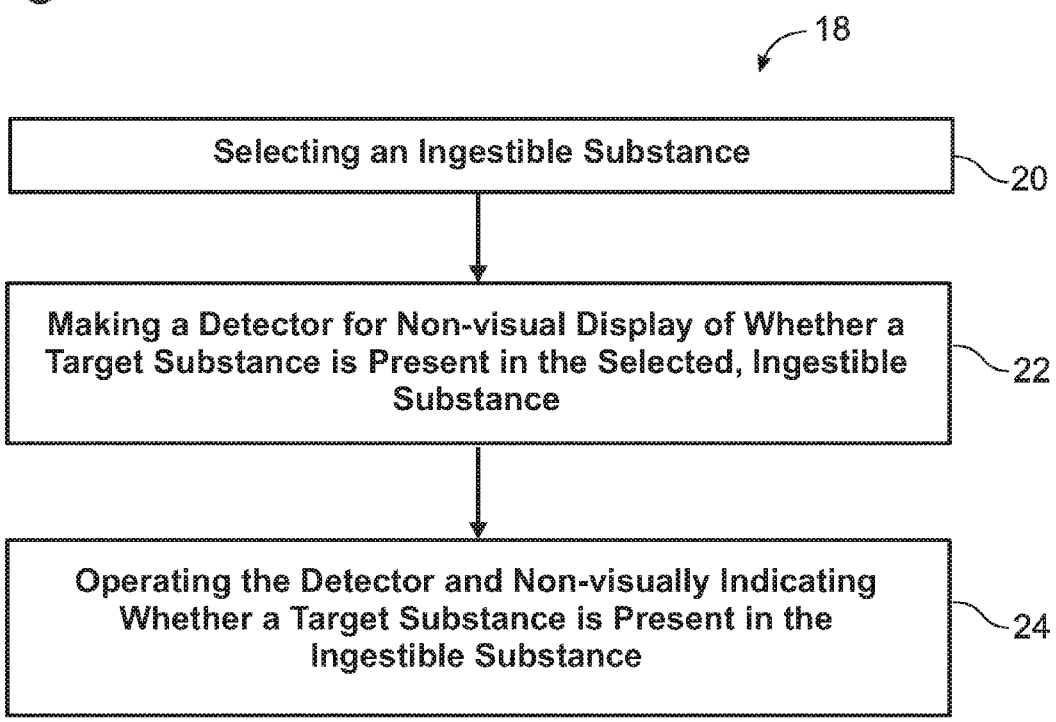
FIG. 2 is a flowchart depicting a non-visual verification method, according to another selected embodiment of the invention.

A second embodiment of the present method is depicted as flowchart 18 in FIG. 2. The method of FIG. 2 includes selecting an ingestible substance, at 20; making a detector for non-visual display of whether a target substance is present in the selected, ingestible substance, at 22; and operating the detector and non-visually indicating whether a target substance is present in the ingestible substance, at 24.

Figure 3:
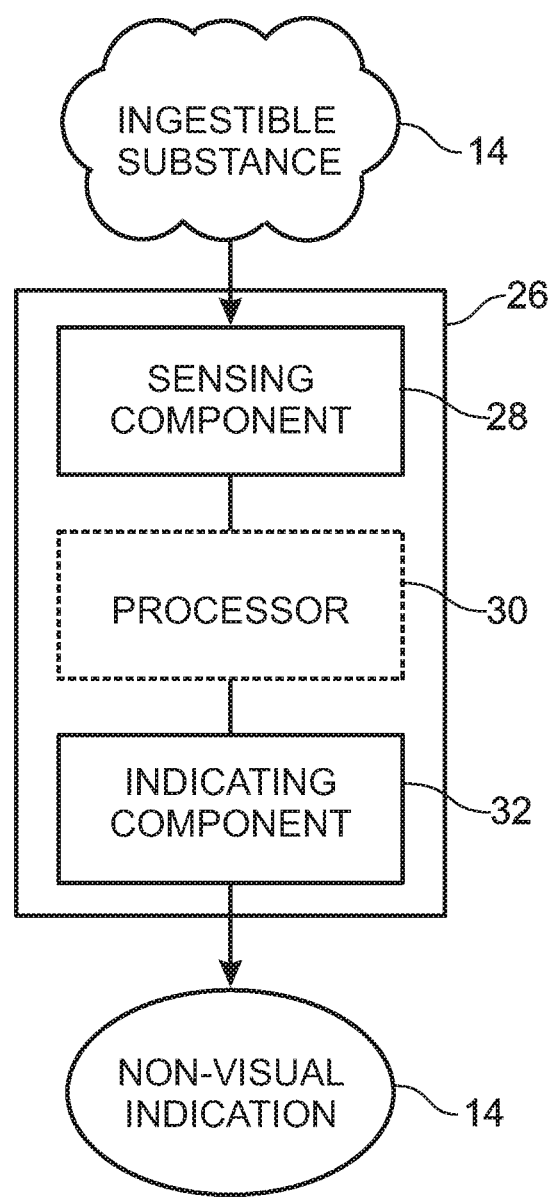
FIG. 3 is a schematic depiction of a non-visual verification system, according to yet another selected embodiment of the invention.

The disclosed methods may be performed using a non-visual verification system 26, as depicted schematically in FIG. 3. The non-visual verification system includes a sensing component 28, and an indicating component at 30. The non-visual verification system optionally further includes a processor 30, as will be discussed below.

The non-visual verification system may be used to test an ingestible substance, prior to consumption, for one or more specific target substances. That target substance(s) is typically an unwanted or undesired substance, such as a drug or a toxin. More particularly, the target substance may be a drug intended to confuse or sedate the consumer. Selected embodiments of the target substance include flunitrazepam, gamma-hydroxybutyric, ketamine, clonazepam, alprazolam, temazepam, and midazolam, without limitation.

The non-visual verification system is typically configured so that the ingestible substance may be tested for the target substance concealably. As used herein, the test is administered concealably where the ingestible substance may be tested for the target substance without alerting bystanders or companions that the test has been administered, or revealing the results of the test.

The non-visual verification system includes a sensing component, where the selected ingestible substance interacts with the system. The sensing component may be as simple as a molecule or a molecular array that incorporates one or more binding sites that are complementary to the target substance, such that binding the target substance results directly or indirectly in a non-visual response.

The ingestible substance to be tested may be any solid, semi-solid, or liquid that is intended for ingestion. The ingestible substance may also be a food or beverage. In one aspect of the invention, the ingestible substance is a liquid or semi-liquid, to facilitate detection of the target substance by chemical or physical interaction. The ingestible substance may also include chewing gum, toothpaste, and other substances that may be placed in the mouth, but not be intended to be swallowed.

The non-visual verification system typically incorporates an indicating component capable of indicating the presence of the selected target substance via a non-visual indication. In one embodiment, the indicating component is directly coupled to the sensing component, such as via molecular recognition, where binding the target substance triggers a molecular modification that produces that desired non-visual indication, such as via a change in flavor, odor, or texture.

In one particular embodiment, the non-visual verification system may correspond to an indicator substance that is selectively reactive toward the target substance (the sensing component), and produces an identifiable flavor compound in the presence of the target substance (the indicating component). Preferably, such substances react with the desired target substance with both selectivity and specificity, so as to avoid false positives. For example, the interaction between an indicator substance and the target substance may be similar to that of specific binding pairs. The indicator substance may be designed so that binding the target substance triggers a molecular rearrangement of the indicator substance, creating a distinct flavor change. Alternatively, or in addition, binding the target substance may trigger the release of one or more small molecules that are then detectable by flavor or odor.

Such an indicator substance may be utilized by placement in the user's mouth, or by placing a component of the non-visual verification system that includes the indicator substance in the user's mouth. Selected embodiments of the indicator substance may produce a bitter, or otherwise identifiable, taste to the user. The indicator substance may include more than one constituent element, and may correspond to any composition, element, material, reagent, or solution, or combination thereof, that is suitable for producing such an identifiable or bitter taste upon reaction with the target substance. In one embodiment, the non-visual verification system incorporates multiple indicator substances, each configured to react selectively with one or more target substances to produce a range of individually identifiable flavors. Such a multi-target system may be useful for the detection of multiple targets of interest simultaneously.

Where the indicating component is intended to produce a non-visual indication that is a flavor, the indicating component may be present on a strip of paper, a dissolvable strip of material, a saliva-dissolvable material, or a chewing gum-type of material, which a user may put in their mouth prior to ingesting the ingestible substance. The substance may also be formulated as a liquid additive packaged in a small container with a dispenser such as a dropper/pipette so that the user can place a drop of the liquid additive in/on the beverage or food, respectively.

An indicator substance configured to create an identifiable or bitter taste when in contact with target substance may be delivered to the user in any suitable form, such as through a pill, a readily-dissolvable tablet, or through a liquid solution. The indicating substance can also be, or be impregnated in, any chewable or edible item that resembles a common beverage or food item, such as a stick or piece of gum, breath mint, mint, candy, such as those candies sold under the federally registered trademark TIC TAC, etc. The substance can therefore be used openly in a manner that would not otherwise alert others that the user is performing a test for the presence of unwanted drugs in a beverage or food item. Alternatively, the substance may be added to the beverage or food itself to produce an identifiable and/or bitter taste.

In some embodiments, the test may include a user placing a non-visual-detector substance in his or her mouth, then drinking the beverage or eating the food in question. The non-visual-detector-detector substance may cause the user to have a pre-selected indicator taste. For example, a user may place a dissolvable strip of material in their mouth to moisten and/or dissolve the strip, thereby releasing the substance. The substance may then coat all or a portion of the interior of the user's mouth, including the taste buds, with the substance, so that the test may be performed by subsequently sipping, ingesting, or tasting a small portion of the suspected beverage or food. The results of the test are therefore fully concealed from others and only known to the taster.

All of the compositions, substances and methods disclosed herein can be made and executed without undue experimentation in light of the present disclosure. While the compositions, substances and methods of this disclosure have been described in terms of preferred embodiments, it will be apparent to those of skill in the art that variations may be applied to the compositions/substances, and in the steps or in the sequence of steps of the method described herein without departing from the concept, spirit and scope of the present disclosure. More specifically, it will be apparent that certain substances that are both chemically and physiologically related may be substituted for the substances described herein while the same or similar results would be achieved. All such similar substitutes and modifications apparent to those skilled in the art are deemed to be within the spirit, scope and concept of the present disclosure.

In an alternative embodiment, the non-visual verification system may correspond to a device that incorporates a sensing component and an indicating component. In this embodiment, the sensing component may incorporate a sample chamber or receptacle, where an aliquot of the ingestible substance to be tested may be inserted for sensing. Alternatively, the sensing component may be configured to be inserted into the ingestible substance, such as a dipstick, test strip, or capillary tube. In one embodiment, the sensing component may include a removable sample collector that is configured to be removed from the non-visual verification system and used to collect an aliquot of the ingestible substance of interest. The sample collector may then be reattached or reinserted into the non-visual verification system for analysis. Alternatively, the non-visual verification system may incorporate one or more stages of sample treatment, such as by the addition of water or other solvent, one or more reagents, and optionally including maceration or mixing in order to facilitate detection of a target substance.

The sensing component may incorporate any of a variety of chemical sensors, electrochemical sensors, spectrometric sensors, pH sensors, and the like. Highly selective detection may be accomplished via the use of enzyme-linked-bound antibodies that bind specifically to selected target substances, and then generate a detectable response via an enzymatic reaction (for example as used in ELISA assays). The sensing component may include only one type of chemical sensor, or may incorporate a plurality of chemical sensors to permit detection of more than one target substance.

Alternatively, the sensing component may utilize one or more microfluidic systems to analyze an ingestible substance for the target substance. Microfluidics permit the manipulation of extremely small volumes of analyte utilizing microfluidic channels having diameters on the order of around 100 nm to several hundred μm. Microfluidic methods include a wide variety of analytical methods, leading to the description of microfluidic methods as 'labs-on-a-chip'.

Where the non-visual verification system incorporates distinct sensing and indicating components, the non-visual verification system may also incorporate a processor 30, as shown in FIG. 3. The processor may correspond to one or more chips, transistors, and processing units configured to receive data originating from the sensing component, evaluating the sensing data, and triggering the indicator component to create the appropriate non-visual indication.

Where the indicating component incorporates a physical indicator that responds to instructions from the processor, the indicating component may generate any of a variety of possible non-visual indications, including smell, touch and sound. For example, the indicating component may be configured to release an appropriate fragrance upon detection of a particular target substance. Alternatively, the indicating component may include a tactile indicator portion, either affixed to the non-visual verification system, or configured to be used remotely. The tactile indicator may be configured to alert the user by vibrating, administering a gentle electrical shock to the user's skin, or applying localized heating, for example. When used remotely, the tactile indicator may take the form of a patch or adhesive button that can be removably affixed to the user's skin, for example under clothing, and then activated by the non-visual verification system. Remote communication between the non-visual verification system and the tactile indicator may be accomplished using radio transmissions, among other methods. A sound indicator could also be used that responds to, for example, a chemical reaction by emitting a sound to indicate that the target substance is present in the ingestible substance.

EXAMPLES

The following example describes an exemplary screening process for an appropriate non-visual-detector substance. This example is intended for illustration and should not be interpreted as limiting the entire scope of the present disclosure.

Example 1

Designing a Detector Substance for ROHYPNOL

Flunitrazepam (ROHYPNOL, NARCOZEP) is a benzodiazepine derivative, and thus contains the core chemical structure characteristic of all benzodiazepines. Flunitrazepam is specifically classed as a nitro-benzodiazepine, and it is the fluorinated methylamino derivative of nitrazepam, another benzodiazepine derivative. Flunitrazepam is characterized by the presence of a fluoro substituent attached to a pendant phenyl substituent.

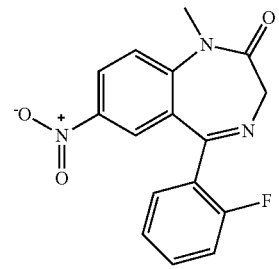

The Chemical Formula for Flunitrazepam

A first criteria for an appropriate non-visual-detector substance is that the reagent should be safe for human consumption at effective concentrations. A second criteria is that it possess an appropriate cross-reactivity with flunitrazepam. A third criteria is that non-visual indicators such as taste and/or smell associated with the resulting adduct compound should be readily detectable by an animal or human consumer of the adduct compound. A fourth criteria is that the non-visual indicators are readily distinctive to an animal or human consumer.

Safe for Consumption

Reactants are to be consumed and, as a result, they must be safe for human consumption when present in the final product. To ensure that reagents are safe for human consumption, only those compounds present in the EAFUS (Everything Added to Food in the United States) database and GRAS (Generally Recognized as Safe) database according to the U.S. Food and Drug Administration are considered as candidates for detector substances.

Appropriate Cross-Reactivity

Selected compound databases were screened by evaluating their potential reactivity towards flunitrazepam. Substances that reacted with flunitrazepam only under strong reaction conditions or in the presence of catalysts were deemed unsuitable candidates, as the detector substance is required to cross-react with flunitrazepam in a beverage. As a result, aromatic substitution at the fluorine substituent was targeted as being likely to succeed.

An analysis of scientific literature indicated that compounds substituted with an amine (—NH) or thiol (—SH) substituent were likely to react with flunitrazepam in the expected conditions. The theoretical reaction mechanism is shown below in Scheme I, assuming that the reaction occurs at room temperature in the presence of ethanol as a solvent, where ethanol is present in a mixed drink or cocktail.

Scheme I

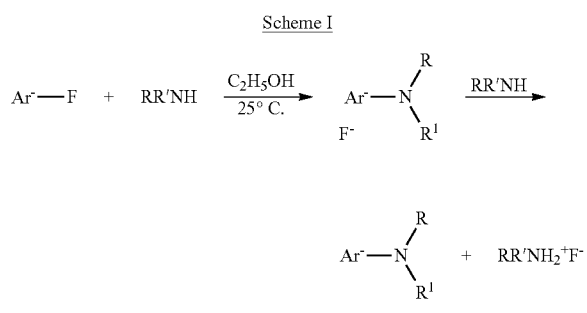

Screening of the EAFUS and FRAS databases resulted in the identification of about 66 compounds comprising 23 primary or secondary amines and 43 thiol compounds.

The structure of the adduct resulting from the reaction of each candidate with flunitrazepam was generated using a LeadGrow tool for virtual library generation from VLifeMDS4.3. The generated adducts were energy minimized using the MMFF force field until a convergence criterion of 0.0001 kcal/mol was achieved. The geometry of the resulting energy-minimized compounds was used to evaluate the predicted flavor and aroma of the generated adducts.

Prediction of Product Taste or Smell

The flavor and aroma of the computationally-generated flunitrazepam adducts were predicted using a QSAR Model. QSARs (Quantitative Structure Activity Relationships) are mathematical models that may be used to predict the physical characteristics of a compound from its chemical structure (known as molecular descriptors). In the QSAR model used, the following parameters were used:

TABLE 1

Parameters used to evaluate flavor

| Model No. | Descriptors | q2 | Pred_r2 | K nearest neighbour | % Prediction accuracy (training/test) # |
|---|---|---|---|---|---|
| 1 | H-DonorCount k3alpha 6ChainCount HydrogensCount | 0.94 | 0.95 | 4 | 94/95 |
| 2 | 4ChainCount 6ChainCount HydrogensCount slogp SdOcount chiV3chain | 0.95 | 0.84 | 4 | 95/84 |

TABLE 2

Descriptor Definitions for Table 1

| Descriptor | Definition |
|---|---|
| H-DonorCount | The number of Hydrogen bond donors present in the molecules |
| k3 alpha | This descriptor signifies third alpha modified kappa shape index |
| 6ChainCount | This descriptor gives total number of six membered rings present in a compound |
| HydrogensCount | The number of hydrogen atoms present in the molecule |
| 4ChainCount | This descriptor signifies total number four membered rings in a compound |
| slogp: | This is log of the octanol/water partition coefficient |
| SdOcount | This descriptor defines the total number of oxygen connected with one double bond |
| chiV3chain | This descriptor signifies atomic valence connectivity index for three membered ring. |

TABLE 3

Parameters used to evaluate aroma

| Model No. | Descriptors | Q2 | Pred_r2 | K nearest neighbour | % Prediction accuracy (training/test) # |
|---|---|---|---|---|---|
| 1 | T_C_O_2 T_2_O_6 T_T_O_6 Epsilon4 T_2_N_1 | 0.87 | 0.64 | 2 | 87/64 |
| 2 | T_2_O_0 chiV4pathCluster DeltaEpsilonA T_2_O_6 SsIE-index | 0.83 | 0.64 | 4 | 83/64 |

TABLE 4

Descriptor Definitions for Table 3

| Descriptor | Definition |
|---|---|
| T_C_O_2 | Number of Carbon atoms separated from Oxygen atom by 2 bonds in the molecule |
| T_2_O_6 | Number of double bonded atoms separated from Oxygen atoms by 6 bonds in the molecule |
| T_T_O_6 | The count of number of atoms present at a bond distance of 6 from any Oxygen atom in the molecule |
| Epsilon4 | Measure of electronegative atom count including hydrogen atoms with respect to the saturated hydrocarbon(reference alkane) created from the molecule/fragment under consideration |
| T_2_N_1 | Number of double bonded atoms separated from any Nitrogen atom by a single bond in the molecule |
| T_2_O_0 | Number of Oxygen atoms with a double bond present in the molecule |
| chiV4pathCluster | This descriptor signifies valence molecular connectivity index of 4th order pathcluster. |
| DeltaEpsilonA | A measure of contribution of unsaturation and electronegative atom count |

Adducts were subjected to taste and smell predictions using QSAR models that employed the descriptors defined above. The resultant adducts were sorted based upon the reliability of the predictions. The adducts provided in Table 5 are predicted to have a strong off-taste, while the adducts provided in Table 6 are predicted to have a strong musk smell, which would be unlikely to remain undetected even when the user is under the influence of alcohol.

TABLE 5

Adducts Predicted to have Strong Flavor

| Cpd. No. | Reagent | Structure of Adduct | Chemical Name |
|---|---|---|---|
| 1 | HS-CH2CH2CH2-CH3 | (structure) | 5-[2-(butylsulfanyl)phenyl]-1-methyl-7-nitro-1,3-dihydro-2H-1,4-benzodiazepin-2-one |
| 2 | (CH3)2CHCH2-SH | (structure) | 1-methyl-5-{2-[(2-methylpropyl)sulfanyl]phenyl}-7-nitro-1,3-dihydro-2H-1,4-benzodiazepin-2-one |
| 3 | cyclopentyl-SH | (structure) | 5-[2-(cyclopentylsulfanyl)phenyl]-1-methyl-7-nitro-1,3-dihydro-2H-1,4-benzodiazepin-2-one |
| 4 | (CH3)2NH | (structure) | 5-[2-(dimethylamino)phenyl]-1-methyl-7-nitro-1,3-dihydro-2H-1,4-benzodiazepin-2-one |
| 5 | H2N-CH2CH2-NH2 | (structure) | 5-{2-[(2-aminoethyl)amino]phenyl}-1-methyl-7-nitro-1,3-dihydro-2H-1,4-benzodiazepin-2-one |

TABLE 5-continued

Adducts Predicted to have Strong Flavor

| Cpd. No. | Reagent | Structure of Adduct | Chemical Name |
|---|---|---|---|
| 6 |  | 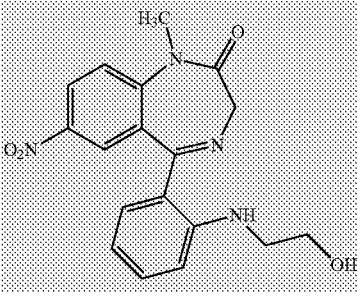 | 5-{2-[(2-hydroxyethyl)amino]phenyl}-1-methyl-7-nitro-1,3-dihydro-2H-1,4-benzodiazepin-2-one |
| 7 | 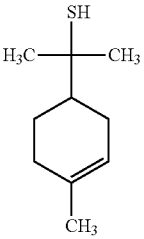<br>Grapefruit Mercaptan | 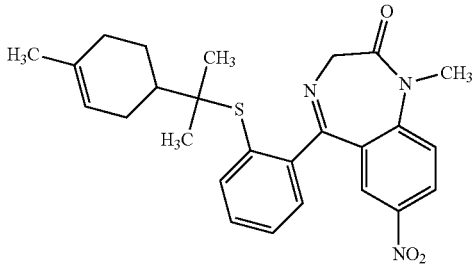 | 1-methyl-5-(2-{[2-(4-methylcyclohex-3-en-1-yl)propan-2-yl]sulfanyl}phenyl)-7-nitro-2,3-dihydro-1H-1,4-benzodiazepin-2-one |
| 8 | 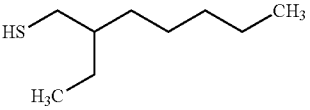 | 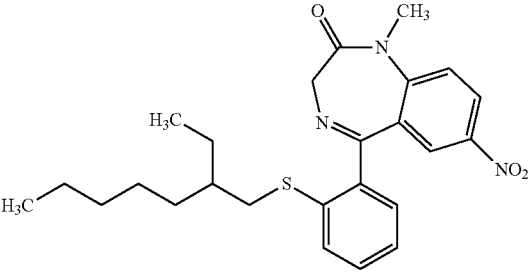 [SMILES: CCCCCC(CC)CSc1ccccc1C1=NCC(=O)N(C)c2ccc([N+](=O)[O-])cc21] | 5-{2-[(2-ethylheptyl)sulfanyl]phenyl}-1-methyl-7-nitro-2,3-dihydro-1H-1,4-benzodiazepin-2-one |
| 9 | 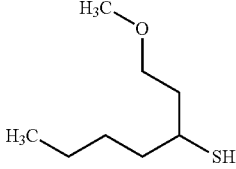 | 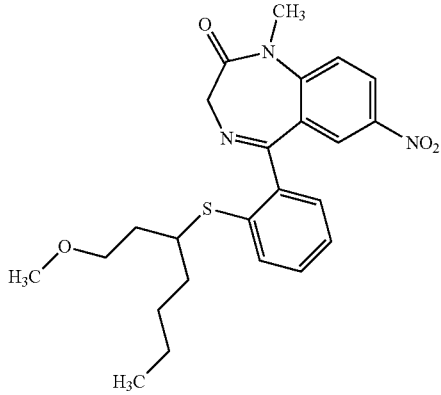 [SMILES: CCCCC(CCOC)Sc1ccccc1C1=NCC(=O)N(C)c2ccc([N+](=O)[O-])cc21] | 5-{2-[(1-methoxyheptan-3-yl)sulfanyl]phenyl}-1-methyl-7-nitro-2,3-dihydro-1H-1,4-benzodiazepin-2-one |

TABLE 5-continued

Adducts Predicted to have Strong Flavor

| Cpd. No. | Reagent | Structure of Adduct | Chemical Name |
|---|---|---|---|
| 10 | H₃C-C(=O)-CH₂-CH₂-SH | | 1-methyl-7-nitro-5-{2-[(3-oxobutyl)sulfanyl]phenyl}-1,3-dihydro-2H-1,4-benzodiazepin-2-one |
| 11 | (CH₃CH₂)₂CH-SH | | 1-methyl-7-nitro-5-[2-(pentan-3-ylsulfanyl)phenyl]-2,3-dihydro-1H-1,4-benzodiazepin-2-one |
| 12 | H₃C-(CH₂)₆-SH | | 5-[2-(heptylsulfanyl)phenyl]-1-methyl-7-nitro-2,3-dihydro-1H-1,4-benzodiazepin-2-one |
| 13 | HOOC-CH₂CH₂CH₂-NH₂ | | 4-{[2-(1-methyl-7-nitro-2-oxo-2,3-dihydro-1H-1,4-benzodiazepin-5-yl)phenyl]amino}butanoic acid |

TABLE 5-continued

Adducts Predicted to have Strong Flavor

| Cpd. No. | Reagent | Structure of Adduct | Chemical Name |
|---|---|---|---|
| 14 | cyclohexylamine (NH$_2$-cyclohexyl) | [structure of 1-methyl-7-nitro benzodiazepinone with 2-(cyclohexylamino)phenyl substituent] | 5-[2-(cyclohexylamino)phenyl]-1-methyl-7-nitro-2,3-dihydro-1H-1,4-benzodiazepin-2-one |

Compounds 1-3 are predicted to possess a strong off-taste by both QSAR models. Compounds 4-6 are predicted to possess a strong off-taste by one of the two QSAR models. Compounds 5-6 are also predicted to possess an off-aroma.

TABLE 6

Adducts Predicted to have Strong Aroma

| Cpd. No. | Reagent | Structure | Chemical Name |
|---|---|---|---|
| 15 | 2,3-dimercaptobutane (H$_3$C-CH(SH)-CH(SH)-CH$_3$) | [structure] | 1-methyl-7-nitro-5-{2-[(3-sulfanylbutan-2-yl)sulfanyl]phenyl}-1,3-dihydro-2H-1,4-benzodiazepin-2-one |
| 16 | 2-methyl-3-mercaptotetrahydrofuran | [structure] | 1-methyl-5-{2-[(2-methyltetrahydrofuran-3-yl)sulfanyl]phenyl}-7-nitro-1,3-dihydro-2H-1,4-benzodiazepin-2-one |

TABLE 6-continued

Adducts Predicted to have Strong Aroma

| Cpd. No. | Reagent | Structure | Chemical Name |
|---|---|---|---|
| 17 | 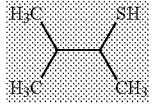 | 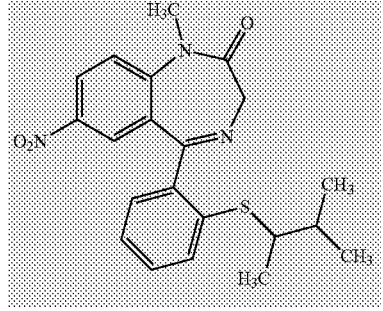 | 1-methyl-5-{2-[(3-methylbutan-2-yl)sulfanyl]phenyl}-7-nitro-2,3-dihydro-1H-1,4-benzodiazepin-2-one |
| 18 | 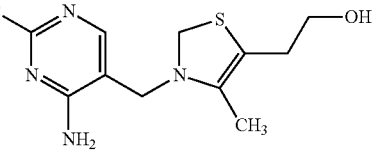 | 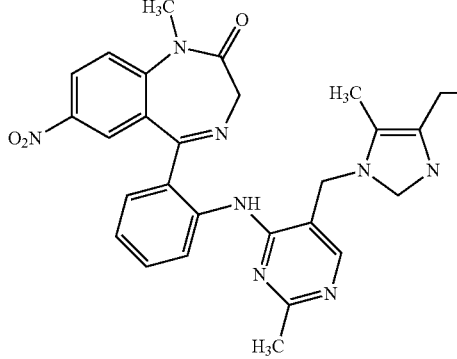 | 5-{2-[(5-{[5-(2-hydroxyethyl)-4-methyl-2,3-dihydro-1,3-thiazol-3-yl]methyl}-2-methylpyrimidin-4-yl)amino]phenyl}-1-methyl-7-nitro-2,3-dihydro-1H-1,4-benzodiazepin-2-one |
| 19 | 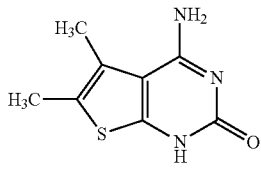 | 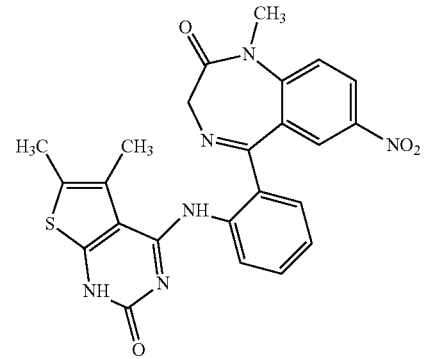 [SMILES: Cc1sc2[nH]c(=O)nc(Nc3ccccc3C3=NCC(=O)N(C)c4ccc([N+](=O)[O-])cc43)c2c1C] | 5-[2-({5,6-dimethyl-2-oxo-1H,2H-thieno[2,3-d]pyrimidin-4-yl}amino)phenyl]-1-methyl-7-nitro-2,3-dihydro-1H-1,4-benzodiazepin-2-one |
| 20 | 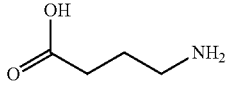 | 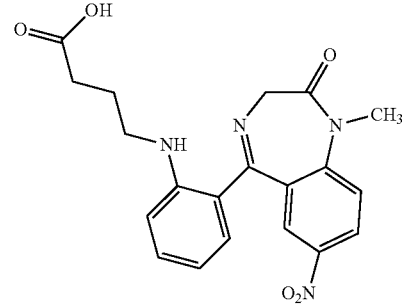 [SMILES: CN1C(=O)CN=C(c2ccccc2NCCCC(=O)O)c2cc([N+](=O)[O-])ccc21] | 4-{[2-(1-methyl-7-nitro-2-oxo-2,3-dihydro-1H-1,4-benzodiazepin-5-yl)phenyl]amino}butanoic acid |

TABLE 6-continued

Adducts Predicted to have Strong Aroma

| Cpd. No. | Reagent | Structure | Chemical Name |
|---|---|---|---|
| 21 | cyclohexylamine (NH₂ on cyclohexane) | 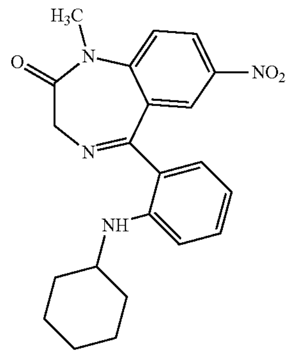 [SMILES: CN1C(=O)CN=C(c2ccccc2NC2CCCCC2)c2cc([N+](=O)[O-])ccc21] | 5-[2-(cyclohexylamino)phenyl]-1-methyl-7-nitro-2,3-dihydro-1H-1,4-benzodiazepin-2-one |
| 22 | isopropylamine | 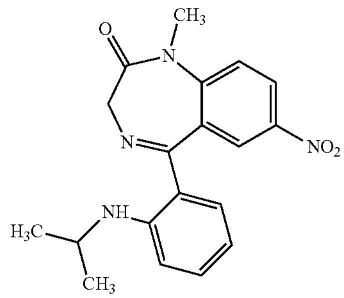 [SMILES: CC(C)Nc1ccccc1C1=NCC(=O)N(C)c2ccc([N+](=O)[O-])cc21] | 1-methyl-7-nitro-5-[2-(propan-2-ylamino)phenyl]-1,3-dihydro-2H-1,4-benzodiazepin-2-one |
| 23 | propylamine | 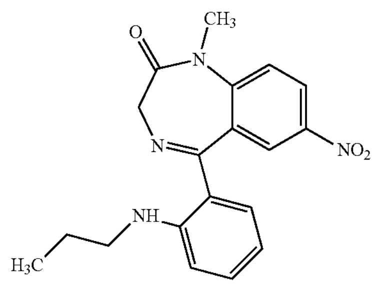 [SMILES: CCCNc1ccccc1C1=NCC(=O)N(C)c2ccc([N+](=O)[O-])cc21] | 1-methyl-7-nitro-5-[2-(propylamino)phenyl]-1,3-dihydro-2H-1,4-benzodiazepin-2-one |

Compound 15-17 are predicted to possess a particularly strong off-aroma by both QSAR models. Compound 18 is predicted to possess a strong off-aroma by one of the two QSAR models. Compounds 15-17 are also predicted to possess an off-taste.

TABLE 7

Toxicity Data for Selected Detector Substances

| Sr No | Reagent | Toxic Dose | Usage dosage |
|---|---|---|---|
| 1 | butane-1-thiol | gavage-rat LD50 1500 mg/kg | 1.00 ppm |
| 2 | 2-methylpropane-1-thiol | gavage-rat LD50 7168 mg/kg oral-rat LD50 7168 mg/kg | Not determined |
| 3 | cyclopentanethiol | oral-mouse LD50 [sex: M, F (5/group)] 2680 mg/kg | 2.00 ppm |
| 4 | N-methylmethanamine | oral-rat LD50 698 mg/kg | — |
| 5 | ethane-1,2-diamine | oral-rat LD50 1200 mg/kg oral-mouse LD50 1000 mg/kg | — |
| 6 | 2-aminoethanol | oral-rat LD50 1720 mg/kg | — |
| 7 | 1-p-menthene-8-thiol | — | — |
| 8 | 2-ethylheptane-1-thiol | — | — |
| 9 | 1-methoxyheptane-3-thiol | — | 0.003 mg/kg |
| 10 | 4-sulfanylbutan-2-one | — | — |
| 11 | pentane-3-thiol | — | 0.020 mg/kg |

TABLE 7-continued

Toxicity Data for Selected Detector Substances

| Sr No | Reagent | Toxic Dose | Usage dosage |
|---|---|---|---|
| 12 | heptane-1-thiol | — | 0.40 mg/kg |
| 13 | 4-aminobutanoic acid | oral-mouse LD50 12680 mg/kg mouse LD50 7230 mg/kg | 50 mg/kg |
| 14 | cyclohexanamine | oral-rat LD50 11 mg/kg LD50 224 mg/kg | — |
| 15 | butane-2,3-dithiol | — | — |
| 16 | 2-methyltetrahydrofuran-3-thiol | gavage-mouse LD50 1860 mg/kg | 5.00 ppm |
| 17 | 3-methylbutane-2-thiol | gavage-rat LD50 [sex: M, F] 540 mg/kg | 2.00 ppm |
| 18 | 2-{3-[(4-amino-2-methylpyrimidin-5-yl)methyl]-4-methyl-2,3-dihydro-1,3-thiazol-5-yl}ethanol | — | — |
| 19 | 4-amino-5,6-dimethylthieno[2,3-d]pyrimidin-2-one | — | — |
| 20 | 4-aminobutanoic acid | oral-mouse LD50 12680 mg/kg mouse LD50 7230 mg/kg | 50 mg/kg |
| 21 | cyclohexanamine | oral-rat LD50 11 mg/kg LD50 224 mg/kg | — |
| 22 | propan-2-amine | oral-rat LD50 111 mg/kg mammal (species unspecified) LD50 500 mg/kg | 2 mg/kg |
| 23 | propan-1-amine | oral-rat LD50 370 mg/kg mammal (species unspecified) LD50 580 mg/kg | 1 mg/kg |

The following numbered paragraphs describe additional aspects and features of the non-visual indicators and indication methods of the present disclosure. Each of these numbered paragraphs can be combined with one or more other paragraphs, and/or with disclosure from elsewhere in this disclosure, including the materials incorporated by reference, in any suitable manner.

1. A non-visual indication method for the presence of flunitrazepam, comprising:
   selecting an ingestible substance;
   non-visually indicating whether flunitrazepam is present in the ingestible substance by using an indicator, chosen from the group consisting of a taste indicator that produces a taste to a user in the presence of flunitrazepam and a smell indicator that produces a smell to a user in the presence of flunitrazepam.

2. The method of paragraph 1, wherein the indicating step involves using a taste indicator that produces a taste to a user, wherein the taste indicator comprises one or more of butane-1-thiol, 2-methylpropane-1-thiol, cyclopentanethiol, N-methylmethanamine, ehtane-1,2-diamine, 2-aminoethanol, 1-p-menthene-8-thiol, 2-ethylheptane-1-thiol, 1-methoxyheptane-3-thiol, 4-sulfanylbutan-2-one, pentane-3-thiol, heptane-1-thiol, 4-aminobutanoic acid, and cyclohexanamine.

3. The method of paragraph 1, wherein the indicating step involves using a taste indicator that produces a taste to a user, wherein the taste indicator comprises one or more of butane-1-thiol, 2-methylpropane-1-thiol, cyclopentanethiol, N-methylmethanamine, ehtane-1,2-diamine, and 2-aminoethanol.

4. The method of paragraph 1, wherein the indicating step involves using a smell indicator that produces a smell to a user, wherein the smell indicator comprises one or more of butane-2,3-dithiol, 2-methyltetrahydrofuran-3-thiol, 3-methylbutane-2-thiol, 2-{3-[(4-amino-2-methylpyrimidin-5-yl)methyl]-4-methyl-2,3-dihydro-1,3-thiazol-5-yl}ethanol, 4-amino-5,6-dimethylthieno[2,3-d]pyrimidin-2-one, 4-aminobutanoic acid, cyclohexanamine, propan-2-amine, and propan-1-amine.

5. The method of paragraph 1, wherein the indicating step involves using a smell indicator that produces a smell to a user, wherein the smell indicator comprises one or more of butane-2,3-dithiol, 2-methyltetrahydrofuran-3-thiol, 3-methylbutane-2-thiol, and 2-{3-[(4-amino-2-methylpyrimidin-5-yl)methyl]-4-methyl-2,3-dihydro-1,3-thiazol-5-yl}ethanol.

6. A non-visual verification system, comprising:
   a non-visual, sensing mechanism constructed to verify whether flunitrazepam is present in an ingestible substance by producing a non-visual indicator that can be understood by a user;
   wherein the sensing mechanism is constructed to produce an indicator to the user that is chosen from the group consisting of a taste indicator and a smell indicator; and
   wherein the sensing mechanism comprises one or more of butane-1-thiol, 2-methylpropane-1-thiol, cyclopentanethiol, N-methylmethanamine, ehtane-1,2-diamine, 2-aminoethanol, 1-p-menthene-8-thiol, 2-ethylheptane-1-thiol, 1-methoxyheptane-3-thiol, 4-sulfanylbutan-2-one, pentane-3-thiol, heptane-1-thiol, 4-aminobutanoic acid, cyclohexanamine, butane-2,3-dithiol, 2-methyltetrahydrofuran-3-thiol, 3-methylbutane-2-thiol, 2-{3-[(4-amino-2-methylpyrimidin-5-yl)methyl]-4-methyl-2,3-dihydro-1,3-thiazol-5-yl}ethanol, 4-amino-5,6-dimethylthieno[2,3-d]pyrimidin-2-one, 4-aminobutanoic acid, cyclohexanamine, propan-2-amine, and propan-1-amine.

7. The system of paragraph 6, wherein the sensing mechanism is also constructed to be concealable so that the user can limit observation of the indicator by others.

8. The system of paragraph 6, wherein the sensing mechanism is constructed to produce a taste indicator to the user and comprises one or more of butane-1-thiol, 2-methylpropane-1-thiol, cyclopentanethiol, N-methylmethanamine, ehtane-1,2-diamine, 2-aminoethanol, 1-p-menthene-8-thiol, 2-ethylheptane-1-thiol, 1-methoxyheptane-3-thiol, 4-sulfanylbutan-2-one, pentane-3-thiol, heptane-1-thiol, 4-aminobutanoic acid, and cyclohexanamine.

9. The system of paragraph 6, wherein the sensing mechanism is constructed to produce a smell indicator to the user and comprises one or more of butane-2,3-dithiol, 2-methyltetrahydrofuran-3-thiol, 3-methylbutane-2-thiol, 2-{3-[(4-amino-2-methylpyrimidin-5-yl)methyl]-4-methyl-2,3-dihydro-1,3-thiazol-5-yl}ethanol, 4-amino-5,6-dimethylthieno[2,3-d]pyrimidin-2-one, 4-aminobutanoic acid, cyclohexanamine, propan-2-amine, and propan-1-amine.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A non-visual indication method, comprising:
   selecting an ingestible substance;
   choosing a non-visual indicator for a target substance from the group consisting of a taste indicator that produces a taste to a user and a smell indicator that produces a smell to a user;
   adding the non-visual indicator to the ingestible substance to cause interaction between the non-visual indicator and the target substance, if the target substance is present in the ingestible substance; and
   non-visually indicating whether the target substance is present in the ingestible substance based upon whether a taste or smell is caused by the interaction.

2. The method of claim 1, wherein the indicating step involves using a taste indicator that produces a taste to a user.

3. The method of claim 1, wherein the indicating step involves using a smell indicator that produces a smell to a user.

4. A non-visual indication method, comprising:
   selecting an ingestible substance;
   choosing a non-visual indicator for a target substance from the group consisting of a taste indicator that produces a taste to a user and a smell indicator that produces a smell to a user;
   adding the non-visual indicator to the ingestible substance to cause interaction between the non-visual indicator and the target substance, if the target substance is present in the ingestible substance; and
   non-visually and concealably indicating whether the target substance is present in the ingestible substance based upon whether a taste or smell is caused by the interaction.

5. The method of claim 4, wherein the non-visually and concealably indicating step involves using a taste indicator that produces a taste to a user.

6. The method of claim 4, wherein the non-visually and concealably indicating step involves using a smell indicator that produces a smell to a user.

7. A non-visual verification system, comprising:
   a non-visual, sensing mechanism constructed to verify whether a target drug is present in an ingestible substance by producing a non-visual indication that can be understood by a user, wherein the sensing mechanism is constructed to produce the non-visual indication to the user, chosen from the group consisting of a taste and a smell, by adding a non-visual indicator to the ingestible substance and by causing interaction between the non-visual indicator and the target substance, if the target substance is present in the ingestible substance.

8. The system of claim 7, wherein the sensing mechanism is also constructed to be concealable so that the user can limit observation of the indication by others.

9. The system of claim 7, wherein the sensing mechanism is constructed to produce a taste to the user.

10. The system of claim 7, wherein the sensing mechanism is constructed to produce a smell to the user.

11. A non-visual verification device, comprising:
    a non-visual, sensing component constructed to verify whether a target drug is present in an ingestible substance by producing a non-visual indication that can be understood by a user, wherein the sensing component is constructed to produce the non-visual indication to the user, chosen from the group consisting of a taste and a smell, by adding a non-visual indicator to the ingestible substance and by causing interaction between the non-visual indicator and the target substance, if the target substance is present in the ingestible substance.

12. The device of claim 11, wherein the sensing component is also constructed to be concealable so that the user can limit observation of the indication by others.

13. The device of claim 11, wherein the sensing component is constructed to produce a taste indication to the user.

14. The device of claim 11, wherein the sensing component is constructed to produce a smell indication to the user.

* * * * *